(12) United States Patent
Lee et al.

(10) Patent No.: US 12,040,071 B2
(45) Date of Patent: *Jul. 16, 2024

(54) METHOD AND PROGRAM FOR PROVIDING FEEDBACK ON SURGICAL OUTCOME

(71) Applicants: HUTOM INC, Seoul (KR); UIF (UNIVERSITY INDUSTRY FOUNDATION), YONSEI UNIV., Seoul (KR)

(72) Inventors: Jong Hyuck Lee, Seongnam-si (KR); Woo Jin Hyung, Seoul (KR); Hoon Mo Yang, Gunpo-si (KR); Ho Seung Kim, Yongin-si (KR)

(73) Assignees: HUTOM INC., Seoul (KR); UIF (UNIVERSITY INDUSTRY FOUNDATION), YONSEI UNIV., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/194,067

(22) Filed: Mar. 31, 2023

(65) Prior Publication Data

US 2023/0238109 A1  Jul. 27, 2023

Related U.S. Application Data

(63) Continuation of application No. 16/914,141, filed on Jun. 26, 2020, now Pat. No. 11,636,940, which is a
(Continued)

(30) Foreign Application Priority Data

Dec. 28, 2017  (KR) .......................... 10-2017-0182889

(51) Int. Cl.
G16H 20/40 (2018.01)
A61B 34/10 (2016.01)
(Continued)

(52) U.S. Cl.
CPC ............. *G16H 20/40* (2018.01); *A61B 34/10* (2016.02); *A61B 34/37* (2016.02); *A61B 90/36* (2016.02);
(Continued)

(58) Field of Classification Search
CPC ........ G16H 20/40; G16H 50/70; G16H 30/40; G16H 50/20; G16H 40/20; G16H 50/50;
(Continued)

(56) References Cited

U.S. PATENT DOCUMENTS

2011/0119224 A1  5/2011  Mangione-Smith
2017/0221385 A1  8/2017  Reiley et al.
(Continued)

FOREIGN PATENT DOCUMENTS

JP    2000-166927 A    6/2000
KR   10-2012-0046439 A   5/2012
(Continued)

OTHER PUBLICATIONS

Saunders, Barry Ferguson, CT suite: The work of diagnosis in the age of noninvasive cutting, ProQuest Dissertations and Theses ProQuest Dissertations Publishing. (2001), (Year: 2001).*
(Continued)

*Primary Examiner* — Amber A Misiaszek
(74) *Attorney, Agent, or Firm* — Studebaker & Brackett PC

(57) ABSTRACT

A method for providing a feedback on a surgical outcome by a computer includes dividing, by the computer, actual surgical data obtained in an actual surgical process into a plurality of detailed surgical operations to obtain actual surgical cue sheet data composed of the plurality of detailed surgical operations, obtaining, by the computer, reference cue sheet data about the actual surgery, and comparing, by the computer, the actual surgical cue sheet data with the
(Continued)

reference cue sheet data, and providing, by the computer, the feedback based on the comparison result.

11 Claims, 4 Drawing Sheets

Related U.S. Application Data continuation of application No. PCT/KR2018/010329, filed on Sep. 5, 2018.

(51) Int. Cl.
    *A61B 34/37*     (2016.01)
    *A61B 90/00*     (2016.01)
    *G16H 50/70*     (2018.01)

(52) U.S. Cl.
    CPC ........ *G16H 50/70* (2018.01); *A61B 2034/107* (2016.02); *A61B 2090/364* (2016.02)

(58) Field of Classification Search
    CPC ........ G16H 30/00; A61B 34/10; A61B 34/37; A61B 90/36; A61B 2034/107; A61B 2090/364; A61B 2034/256; A61B 34/30; A61B 2017/00119; A61B 90/361; A61B 2034/101; A61B 2034/105; A61B 2090/365; A61B 2034/2065; A61B 34/20

See application file for complete search history.

(56) References Cited

U.S. PATENT DOCUMENTS

| | | | |
|---|---|---|---|
| 2017/0258526 A1* | 9/2017 | Lang | ............... A61B 17/157 |
| 2018/0233222 A1* | 8/2018 | Daley | ............... G16H 50/50 |
| 2019/0146458 A1* | 5/2019 | Roh | ............... G16H 30/40 |
| | | | 700/98 |

FOREIGN PATENT DOCUMENTS

| | | |
|---|---|---|
| KR | 10-2012-0126679 A | 11/2012 |
| KR | 10-1302595 B1 | 8/2013 |
| KR | 10-2016-0066522 A | 6/2016 |
| KR | 10-2016-0096868 A | 8/2016 |

OTHER PUBLICATIONS

International Search Report issued in PCT/KR2018/010329; mailed Dec. 11, 2018.

Office Action issued in KR 10-2018-0058609; mailed by the Korean Intellectual Property Office on Feb. 11, 2020.

The extended European search report issued by the European Patent Office on Aug. 20, 2021, which corresponds to European Patent Application No. 18896154.4-1126 and is related to U.S. Appl. No. 16/914,141.

\* cited by examiner

METHOD AND PROGRAM FOR PROVIDING FEEDBACK ON SURGICAL OUTCOME

CROSS-REFERENCE TO RELATED APPLICATIONS

The present application is a Continuation of U.S. patent application Ser. No. 16/914,141 filed Jun. 26, 2020, which is a continuation of International Patent Application No. PCT/KR2018/010329, filed on Sep. 5, 2018, which is based upon and claims the benefit of priority to Korean Patent Application No. 10-2017-0182889, filed on Dec. 28, 2017. The disclosures of the above-listed applications are hereby incorporated by reference herein in their entirety.

BACKGROUND

Embodiments of the inventive concept described herein relate to a method and a program for providing a feedback on a surgical outcome.

There is a need to develop a scheme capable of providing information to assist a surgeon in a surgical process. In order to provide the information to assist with the surgery, detailed surgical operations of the surgery must be recognized.

Conventionally, in order to design a scenario for optimizing the surgical process, a medical image that is previously captured is referred to or an advice from a highly skilled surgeon is referred. However, it is difficult to determine unnecessary processes only based on the medical image, and the advice of the experienced surgeon is not customized to a specific patient.

Therefore, the medical image or the advice of the skilled surgeon may not be utilized as auxiliary means for optimizing the surgical process for a surgery target patient as a surgery target.

Accordingly, development of a method for minimizing unnecessary processes in performing the surgery using a 3D medical image (for example, virtual images of 3D surgical tool movements and internal organ changes caused by the movement of the tool) to optimize the surgical process, and providing surgery assisting information based on the optimized surgical process is required.

Further, recently, deep learning has been widely used for analysis of medical images. Deep learning is defined as a set of machine-learning algorithms that attempt high-level abstractions (abstracting of key content or functions in a large amount of data or complex data) via a combination of several nonlinear transformation schemes. Deep learning may be largely considered as a field of machine learning that teaches a human mindset to a computer.

SUMMARY

Embodiments of the inventive concept provide a method and a program for providing a feedback on a surgical outcome.

Purposes that the inventive concept intends to achieve are not limited to those mentioned above. Other purposes as not mentioned will be clearly understood by those skilled in the art from following descriptions.

According to an exemplary embodiment, a method for providing a feedback on a surgical outcome by a computer includes dividing, by the computer, actual surgical data obtained in an actual surgical process into a plurality of detailed surgical operations to obtain actual surgical cue sheet data composed of the plurality of detailed surgical operations, obtaining, by the computer, reference cue sheet data about the actual surgery, and comparing, by the computer, the actual surgical cue sheet data with the reference cue sheet data, and providing, by the computer, the feedback based on the comparison result.

Further, the actual surgical data may be divided into the plurality of detailed surgical operations, based on at least one of a surgery target portion, a type of surgical tool, a number of surgical tools, a position of the surgical tool, an orientation of the surgical tool, and movement of the surgical tool included in the actual surgical data.

Further, at least one of a standardized name or standardized code data may be assigned to each of the plurality of detailed surgical operations.

Further, the providing of the feedback may includes obtaining search information used for searching for at least one of the plurality of detailed surgical operations, extracting at least one detailed surgical operation corresponding to the search information based on the standardized name or the standardized code data, and providing a feedback on the extracted at least one detailed surgical operation.

Further, the reference cue sheet data may include optimized cue sheet data about the actual surgery, or referenced virtual surgical cue sheet data.

Further, the providing of the feedback may include comparing the plurality of detailed surgical operations included in the actual surgical cue sheet data with a plurality of detailed surgical operations included in the reference cue sheet data, and determining, based on the comparison result, whether an unnecessary detailed surgical operation, a missing detailed surgical operation, or an incorrect detailed surgical operation is present in the actual surgical cue sheet data.

Further, the determining of whether the incorrect detailed surgical operation is present in the actual surgical cue sheet data may include comparing movement of surgical tool corresponding to a detailed surgical operation included in the reference cue sheet data with movement of surgical tool corresponding to a detailed surgical operation included in the actual surgical cue sheet data, and determining, based on the comparison result, whether the detailed surgical operation included in the actual surgical cue sheet data is incorrect.

Further, the method may further include adding the actual surgical cue sheet data to to-be-learned cue sheet data, obtaining a model for obtaining optimized cue sheet data using the to-be-learned cue sheet data having the actual surgical cue sheet data added thereto, and performing reinforcement learning on the obtained model.

Further, the method may further include detecting at least one surgical error situation from the obtained surgical information, and providing a feedback on the detected surgical error situation.

Further, the method may further include obtaining information about prognosis corresponding to each of one or more actual surgical cue sheet data including the actual surgical cue sheet data, performing reinforcement learning based on the one or more actual surgical cue sheet data and the prognosis information thereof, and determining a correlation between at least one detailed surgical operation included in the one or more actual surgical cue sheet data and the prognosis, based on the reinforcement learning result.

According to an exemplary embodiment, a computer program is stored in a computer-readable storage medium, wherein the computer program is configured to perform the method as defined above in combination with a computer as hardware.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
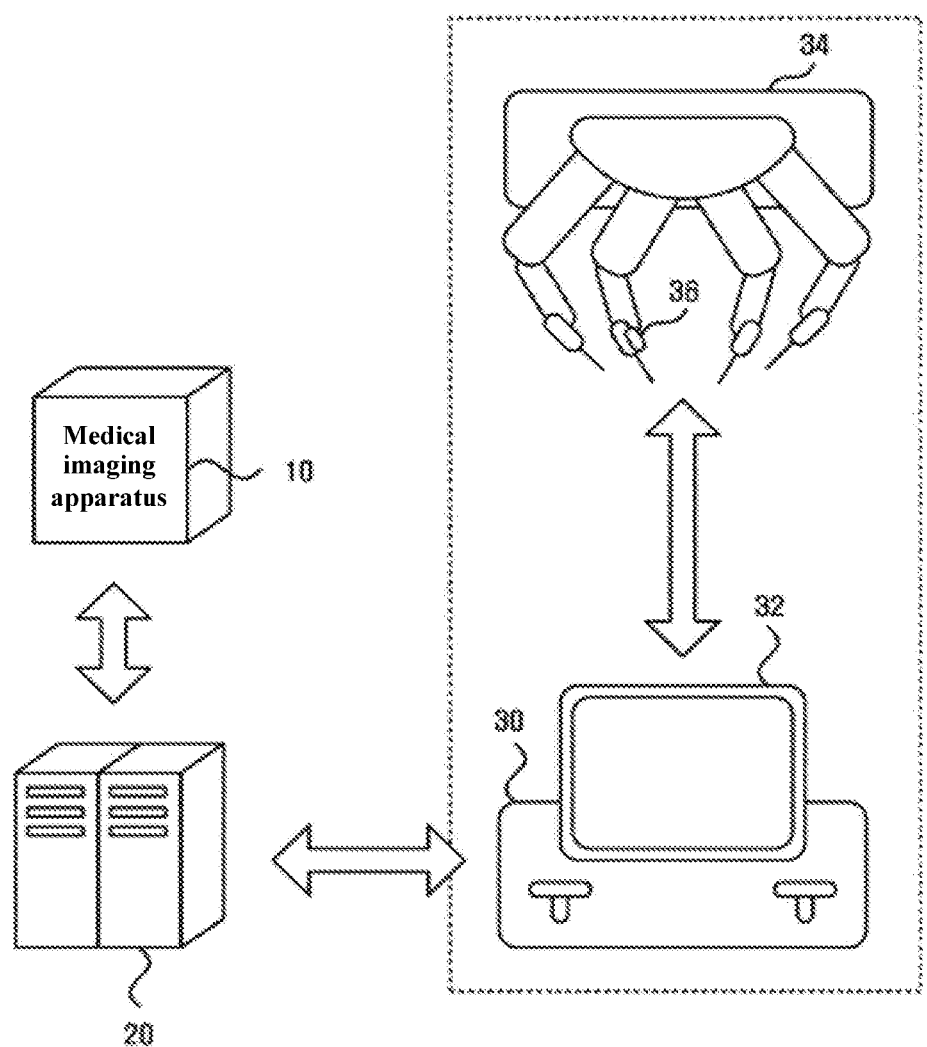
FIG. 1 is a view showing a robot-based surgery system according to the disclosed embodiment.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to inform merely fully those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A term "unit" or "module" used herein means software or a hardware component such as FPGA, or ASIC. The "unit" or "module" performs a predetermined role. However, the "unit" or "module" is not meant to be limited to the software or the hardware. The "unit" or "module" may be configured to reside in an addressable storage medium and may be configured to execute one or more processors. Thus, in an example, the "unit" or "module" includes components such as software components, object-oriented software components, class components and task components, processes, functions, attributes, procedures, subroutines, segments of a program code, drivers, firmware, a microcode, circuitry, data, database, data structures, tables, arrays and variables. Functionality provided within the components and the "units" or "modules" may be combined into a smaller number of components and "units" or "modules" or may be further divided into additional components and "units" or "modules".

As used herein, a term "image" refers to multi-dimensional data composed of discrete image elements (e.g., pixels in a 2D image and voxels in a 3D image). For example, the image may include a medical image of an object obtained by a CT imaging apparatus.

As used herein, the term "object" may be a person or an animal, or a portion or an entirety of a person or animal. For example, the object may include at least one of organs such as a liver, a heart, a uterus, a brain, a breast, and an abdomen, and a blood vessel.

As used herein, a term "user" may be a surgeon, a nurse, a clinical pathologist, a medical image expert, etc. as a medical expert, may be a technician repairing a medical apparatus. However, the present disclosure is not limited thereto.

As used herein, a term "medical image data" refers to a medical image that is captured by a medical imaging apparatus, and includes all medical images that may represent a body of an object in a 3D modelling manner. The "medical image data" may include a computed tomography (CT) image, a magnetic resonance imaging (MRI) image, a positron emission tomography (PET) image, etc.

As used herein, a term "virtual body model" refers to a model created in a conforming manner to an actual patient's body based on the medical image data. The "virtual body model" may be created by modeling the medical image data in a three dimensions manner or by correcting the modeled data to be adapted to an actual surgery situation.

As used herein, a term "virtual surgical data" means data including rehearsal or simulation detailed surgical operation performed on the virtual body model. The "virtual surgical data" may be image data of rehearsal or simulation performed on the virtual body model in a virtual space or may be data in which a surgical operation performed on the virtual body model is recorded.

As used herein, a term "actual surgical data" refers to data obtained as a medical staff performs actual surgery. The "actual surgical data" may be image data obtained by imaging a surgical target portion in an actual surgical process, or may be data in which a surgical operation performed in the actual surgical process is recorded.

As used herein, a term "detailed surgical operation" means a minimum unit of a surgical operation as divided according to specific criteria.

As used herein, a term "cue sheet data" refers to data in which detailed surgical operations into which a specific surgical process is divided are recorded in order.

As used herein, a term "to-be-executed cue sheet data" refers to cue sheet data obtained based on the virtual surgical data obtained via simulation by the user.

As used herein, a term "training virtual surgical cue sheet data" is included in the to-be-executed cue sheet data, and means cue sheet data created based on the virtual surgical data obtained via surgery simulation by the user.

As used herein, a term "referenced virtual surgical cue sheet data" refers to cue sheet data about virtual surgery performed by a specific medical person for construction of to-be-learned big data or surgery process guidance.

As used herein, a term "optimized cue sheet data" means cue sheet data about an optimized surgical process in terms of a surgery time or prognosis.

As used herein, a term "to-be-learned cue sheet data" means cue sheet data used for learning for optimized cue sheet data calculation.

As used herein, a term "surgery guide data" means data used as guide information during actual surgery.

As used herein, a term "computer" includes all of various devices capable of performing computation and providing the computation result to the user. For example, the computer may include not only a desktop (PC) and a notebook, but also a smart phone, a tablet PC, a cellular phone, a PCS (Personal Communication Service) phone, a mobile terminal of synchronous/asynchronous IMT-2000 (International Mobile Telecommunication-2000), a palm personal computer (PC), and a personal digital assistant (PDA). Further, when a head mounted display (HMD) apparatus includes a computing function, the HMD apparatus may be a computer. Further, the computer may be a server that receives a request from a client and performs information processing.

Hereinafter, embodiments of the inventive concept will be described in detail with reference to the accompanying drawings.

FIG. 1 is a view showing a robot-based surgery system according to a disclosed embodiment.

Referring to FIG. 1, a schematic diagram of the system capable of performing robot-based surgery according to the disclosed embodiment is illustrated.

According to FIG. 1, the robot-based surgery system includes a medical imaging apparatus 10, a server 20, and a controller 30, an imaging unit 36, a display 32, and a surgery robot 34 provided in an operating room. According to an embodiment, the medical imaging apparatus 10 may be omitted from the robot-based surgery system according to the disclosed embodiment.

In one embodiment, the robot-based surgery may be performed by the user controlling the surgery robot 34 using the controller 30. In one embodiment, the robot-based surgery may be performed automatically by the controller 30 without the user control.

The server 20 is a computing device including at least one processor and a communication unit.

The controller 30 includes a computing device including at least one processor and a communication unit. In one embodiment, the controller 30 includes hardware and software interfaces for controlling the surgery robot 34.

The imaging unit 36 includes at least one image sensor. That is, the imaging unit 36 includes at least one camera to image a surgery target portion. In one embodiment, the imaging unit 36 is used in conjunction with the surgery robot 34. For example, the imaging unit 36 may include at least one camera coupled with a surgery arm of the surgery robot 34.

In one embodiment, the image captured by the imaging unit 36 is displayed on the display 32.

The controller 30 receives information necessary for surgery from the server 20 or creates information necessary for surgery and provides the information to the user. For example, the controller 30 displays the created or received information necessary for the surgery on the display 32.

For example, the user controls movement of the surgery robot 34 by manipulating the controller 30 while looking at the display 32 to perform robot-based surgery.

The server 20 creates information necessary for robot-based surgery using medical image data of the object (patient) previously imaged by the medical imaging apparatus 10 and provides the created information to the controller 30.

The controller 30 may display the information received from the server 20 on the display 32 to present the information to the user, or may use the information received from the server 20 to control the surgery robot 34.

In one embodiment, imaging means that may be used in the medical imaging apparatus 10 is not limited particularly. For example, various medical imaging means such as CT, X-Ray, PET, and MRI may be used.

Hereinafter, a method for providing a feedback on a surgical outcome will be described in detail with reference to the drawings.

Figure 2:
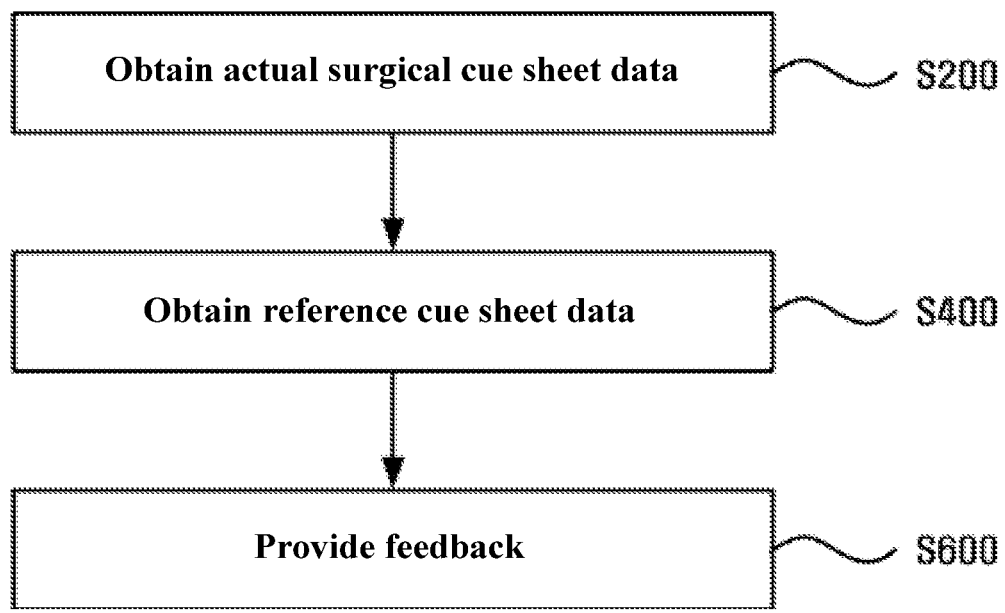
FIG. 2 is a flowchart showing a method for providing a feedback on a surgical outcome according to one embodiment.

FIG. 2 is a flowchart showing a method for providing a feedback on a surgical outcome according to one embodiment.

Steps shown in FIG. 2 may be performed in time series by the server 20 or the controller 30 shown in FIG. 1. Hereinafter, for convenience of description, each step is described as being performed by a computer, but a subject to perform each step is not limited to a specific device. All or some of the steps may be performed by the server 20 or the controller 30.

Referring to FIG. 2, a method for providing a feedback on a surgical outcome according to an embodiment of the present disclosure includes dividing, by the computer, actual surgical data obtained from an actual surgical process into a plurality of detailed surgical operations to obtain actual surgical cue sheet data composed of the plurality of detailed surgical operations (S200); obtaining, by the computer, reference cue sheet data about the actual surgery (S400); and comparing, by the computer, the actual surgical cue sheet data and the reference cue sheet data to provide a feedback based the comparison result (S600). Hereinafter, detailed description of each step will be described.

The computer may divide the actual surgical data obtained from the actual surgical process into the plurality of detailed surgical operations to obtain the actual surgical cue sheet data composed of the plurality of detailed surgical operations (S200). The computer creates the actual surgical cue sheet data based on the surgical image imaged in the surgical process by the surgery robot or based on data obtained in a control process of the surgery robot.

The detailed surgical operation constituting the cue sheet data refers to a minimum operation unit constituting the surgical process. The actual surgical data may be divided into the detailed surgical operations based on several criteria. For example, the actual surgical data may be divided to the detailed surgical operations based on surgery types (e.g., laparoscopic surgery, robot-based surgery), anatomical body parts where surgery is performed, surgical tools as used, a number of surgical tools, an orientation or a position of the surgical tool displayed on a screen, movement of the surgical tool (for example, forward/reward movement), etc.

The division criteria and detailed categories included within the division criteria may be directly set by the medical staff learning the actual surgical data. The computer may perform supervised learning based on the division criteria and the detailed categories set by the medical staff to divide the actual surgical data into the detailed surgical operations as a minimum operation unit.

Further, the division criteria and detailed categories included within the division criteria may be extracted via learning of a surgical image by the computer. For example, the computer may calculate the division criteria and detailed categories included within the division criteria via deep learning (i.e., unsupervised learning) of actual surgical data accumulated as big data. Subsequently, the computer may divide the actual surgical data based on the division criteria created via the learning of the actual surgical data to create the cue sheet data.

Further, in another embodiment, the actual surgical data may be divided based on a result of determining whether the actual surgical data satisfies the division criterion via image recognition. That is, the computer may recognize the anatomical organ position on the screen, the number of surgical tools appearing on the screen, and the number of the surgical tools on the screen within the image of the actual surgical data as the division criterion and may divide the actual surgical data into the detailed surgical operation units based on the recognized division criterion.

Further, in another embodiment, the computer may perform the division process for cue sheet data creation based on surgical tool movement data included in the actual surgical data. The actual surgical data may include various information input in a process of controlling the surgery robot, such as the type and the number of surgical tools selected by the user, information about the movement of each surgical tool when the user performs robot-based surgery. Accordingly, the computer may perform division based on information included in the actual surgical data at each time point thereof.

Further, in one embodiment, the actual surgical data includes various types of detailed surgical operation such as ablation and suture. Division is performed based on the division criteria. Specifically, a process of dividing the actual surgical data (for example, actual surgery image) about the actual gastric cancer surgery into the detailed surgical operations to create the cue sheet data is as follows.

For example, gastric cancer surgery includes a detailed surgical operation to ablate a portion or an entirety of a stomach containing a tumor, and a detailed surgical operation to ablate a lymph node. In addition, various resections and connections are used depending on a state of the gastric cancer. In addition, each detailed surgical operation may be divided into a plurality of detailed surgical operations based on a specific location where the detailed surgical operation is taken and a direction of movement of the surgical tool.

For example, the detailed operation of the gastric cancer surgery may be divided into an opening step, an ablation step, a connection step, and a suture step.

Further, a method of changing a disconnected state of an organ to a connected state includes an in vitro anastomosis method of incising and connecting at least 4 to 5 cm of an end of an anticardium, and an in vivo anastomosis method in which about 3 cm of umbilicus is incised and incision and anastomosis occur in an abdominal cavity. The above-described connection stage may be divided in detailed sub-steps according to the specific connection method as described above.

Furthermore, each surgery operation may be divided into a plurality of detailed surgical operations according to the position and the movement of the surgical tool.

Each of the divided detailed surgical operations has a standardized name allocated thereto based on a location where the detailed surgical operation is performed and a pathway of the surgical tool.

In one embodiment, the standardized name may be variously defined. For example, when dealing with a specific portion as a lower right portion of the stomach, the name of the portion may be a name commonly used in the medical field. More comprehensive or detailed names defined in the system according to the disclosed embodiment may be used.

Therefore, the surgery image about the actual surgery by the user may be organized into information in a form of a cue sheet in which a plurality of detailed surgical operations are sequentially arranged based on the standardized names.

Further, in one embodiment, the cue sheet data may be created as code data of specific digits based on the division criteria for dividing the surgical data into the detailed surgical operations. That is, the computer divides the actual surgical data into standardized detailed surgical operations by applying standardized division criteria and designating detailed categories within the division criteria. The computer may allocate a standardized code value to each detailed category and allocate standardized code data to distinguish each detailed surgical operation.

The computer allocates, to each detailed surgical operation, digitalized code data obtained by allocating numbers or letters to categories in order from a higher category to a lower category to which the specific detailed surgical operations belong, according to the order of application of the division criteria. Thus, the computer may create cue sheet data in a form in which not images of the divided detailed surgical operations but the standardized code data of the detailed surgical operations are listed. Further, the user may share or deliver the actual surgical process by providing only the cue sheet data composed of the standardized code data.

In one embodiment, when the computer is a client terminal disposed in the operating room or corresponds to the controller 30, the computer may acquire the standardized code data from the surgery image, and transmit the obtained code data to the server 20 such that the actual surgical process is shared or delivered.

In one embodiment, when the computer corresponds to the server 20, the surgical image is transmitted to the server 20. Then, the server 20 may create the cue sheet data and the code data.

Further, in one embodiment, the computer may allocate a standardized name to a standardized code of each detailed surgical operation. Thus, the user may select and identify only a desired detailed surgical operation within the entire cue sheet. Further, in this case, the user may easily grasp a progress of the surgery or the rehearsal by simply viewing the cue sheet in which the detailed surgical operations are sequentially arranged based on the standardized names thereof, without viewing an entirety of the surgery image.

The cue sheet data may be converted into a surgical image using an image database for each detailed surgical operation. In the image data base, an image matching each code data may be stored. A plurality of images matching each code data may be stored therein depending on a situation. For example, specific detailed code data may include different detailed surgical operation images in the image database according to previously performed operations.

Further, as each cue sheet data is matched with a specific virtual body model and the matching result is stored, the computer may reproduce the cue sheet data as a surgical simulation image by sequentially applying the detailed surgical operations included in the cue sheet data to the virtual body model.

Therefore, the image corresponding to the cue sheet data may be reproduced in the same point of view as that of the surgery image. Alternatively, the image corresponding to the cue sheet data may be reconstructed in a point of view different from that of the surgery image and the reconstructed image may be reproduced. Alternatively, the image may be modeled in a 3D manner, and thus the viewpoint and a position thereof may be adjusted according to the user's manipulation.

The computer acquires the reference cue sheet data about the actual surgery (S400).

In one embodiment, the reference cue sheet data means optimized cue sheet data created by the computer.

In another embodiment, the reference cue sheet data refers to referenced virtual surgical cue sheet data.

Figure 3:
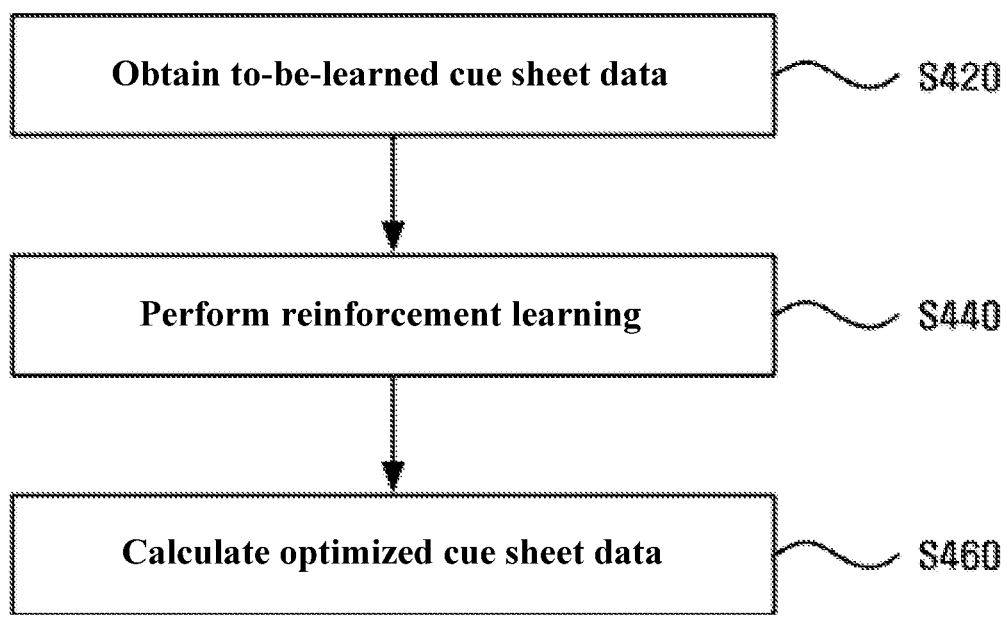
FIG. 3 is a flowchart showing a method for calculating an optimized cue sheet data according to one embodiment.

FIG. 3 is a flowchart showing a method for calculating the optimized cue sheet data according to one embodiment.

The computer acquires one or more to-be-learned cue sheet data (S420). The to-be-learned cue sheet data refers to learning target data that is to be learned for calculation of the optimized cue sheet data. The to-be-learned cue sheet data may include cue sheet data created based on the actual surgical data (i.e. actual surgical cue sheet data) or cue sheet data created based on the simulated actual surgical data for reference (i.e. referenced virtual surgical cue sheet data). The actual surgical cue sheet data is created by the computer dividing the actual surgical data according to the division criteria. The referenced virtual surgical cue sheet data is not obtained in the user's surgery simulation process, but is created by performing simulation for purpose of constructing the learning target data or providing the same to practitioners for reference.

Thereafter, the computer performs reinforcement learning using the to-be-learned cue sheet data (S440). The reinforcement learning refers to one area of the machine learning, and refers to a method in which an agent defined in a certain environment recognizes a current state and selects a detailed surgical operation or a sequence of detailed surgical operations that maximizes reward among selectable detailed surgical operations or sequences thereof. The reinforcement learning may be summarized as learning of a scheme of maximizing compensation based on state transition and compensation according to the state transition.

Then, the computer calculates the optimized cue sheet data using the reinforcement learning result (S460). The optimized cue sheet data is calculated based on the shortest surgical time that may reduce the patient's anesthesia time, a minimum bleeding amount, an essential operation group, and an essential performance sequence, etc. based on the reinforcement learning result.

The essential operation group refers to a group of detailed surgical operations that must be performed together to perform a specific detailed surgical operation. The essential performance sequence refers to a surgical operation sequence at which that operations must be sequentially performed in a course of performing specific surgery. For example, surgical operations that must be performed sequentially and an order thereof may be determined according to the type of surgery or the type of the surgical operation.

Further, the computer may calculate situation-based optimized cue sheet data based on the patient's physical condition, the surgery target portion (e.g., tumor tissue) condition (e.g., a size, a location, etc. of the tumor) thereof the reinforcement learning. To this end, the computer utilizes the patient condition, the surgery target portion condition, and the like along with the to-be-learned cue sheet data for learning.

In one embodiment, the computer may perform virtual simulation surgery on its own. For example, the computer may create a surgical process according to the type of surgery and the type of the patient based on the disclosed surgical process optimizing method, and may perform the virtual surgery simulation based on the created surgical process.

The computer evaluates results of the virtual surgery simulation. The computer may perform the reinforcement learning based on virtual surgical simulation information and evaluation information on the result thereof, thereby to obtain an optimized surgical process.

A model trained to create the optimal surgical process may not create an optimized surgical process according to an individual patient and a type of surgery thereof because in actual surgery, body structures and types of surgery of patients are different from each other.

Therefore, the computer may create a surgical process based on the patient's body structure and the type of surgery thereof using the trained model, and may perform virtual surgery simulation, based on the created surgical process. In this way, the computer may create an optimized surgical process for an individual patient and a type of surgery thereof via the reinforcement learning.

The computer compares the actual surgical cue sheet data and the reference cue sheet data with each other and provides a feedback based on a comparison result (S600).

In one embodiment, the operation of comparing the actual surgical cue sheet data and the reference cue sheet data with each other may be performed by the computer or the controller 30 disposed in the operating room, or may be performed on the server 20.

When the comparison is performed by the server 20, the server 20 acquires the reference cue sheet data, and compares the reference cue sheet data with the surgical image or the cue sheet data (code data) obtained from the controller 30.

When the comparison is performed by the computer or the controller 30 placed in the operating room, the computer acquires the cue sheet data from the surgical image, and compares the cue sheet data with the reference cue sheet data received from the server 20.

In one embodiment, the feedback may be provided through a website or an application. For example, the feedback may be provided through an application installed in a mobile terminal of the surgeon. When the surgery is finished, a notification related to the feedback may be provided to the mobile terminal of the surgeon.

Figure 4:
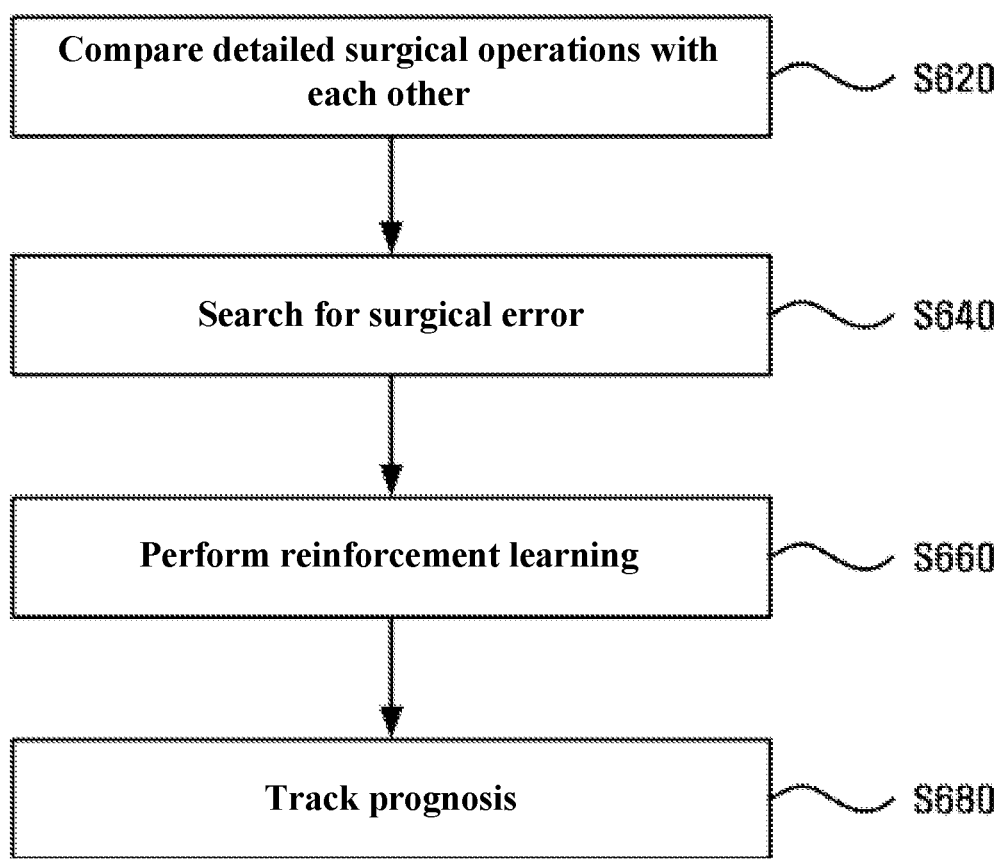
FIG. 4 is a flowchart showing a method for obtaining a feedback according to one embodiment.

FIG. 4 is a flowchart showing a method for obtaining a feedback according to one embodiment.

In one embodiment, the computer may compare a type and an order of detailed surgical operations included in the actual surgical cue sheet data with a type and an order of detailed surgical operations included in the reference cue sheet data, and may provide a feedback on the surgical outcome based on the comparison result (S620).

For example, the computer may determine whether a missing detailed surgical operation, an unnecessary detailed surgical operation, or an incorrect detailed surgical operation among detailed surgical operations included in actual surgical cue sheet data, compared to the detailed surgical operations included in the reference cue sheet data is present, and may provide a feedback on the surgical outcome, based on determination result.

For example, a required detailed surgical operation included in the reference cue sheet data may be omitted from the actual surgical cue sheet data.

Further, an unnecessary detailed surgical operation not included in the reference cue sheet data may have been included in the actual surgical cue sheet data.

Further, a detailed surgical operation included in the reference cue sheet data may be included in the actual surgical cue sheet data, but details thereof may be modified or incorrect.

In this case, the type of the detailed surgical operation in the reference cue sheet data and the type of the detailed surgical operation in the actual surgical cue sheet data are identical with each other, but details thereof may be different from each other.

Thus, the computer determines whether each detailed surgical operation has been performed correctly. Although a specific detailed surgical operation is to be included in an entire surgical process, the specific detailed surgical operation may not be performed normally. For example, when the specific detailed surgical operation is an operation of catching a tissue at a specific location using tongs-shaped surgical tool, the tool may catch the tissue at a deeper position than an optimal depth or the tissue may be caught in a small area of the tongs such that the tissue is caught and then is removed from the tongs. This situation may be determined as the incorrect detailed surgical operation. The computer may recognize the tissue and the surgical tool in the actual surgery image via image recognition to accurately recognize the detailed surgical operation, and may compare the recognized detailed surgical operation with a correct detailed surgical operation in the optimized cue sheet data for evaluation and feedback.

Further, the computer may analyze the actual surgical cue sheet data itself, and provide information on a record of an abnormal situation or an unexpected situation based on the analysis result. For example, when a bleeding occurs in a specific site, the computer may provide at least one of the fact that the bleeding has occurred, a location of the bleeding, or an amount of the bleeding.

Further, the computer may analyze records of the detailed surgical operation included in the actual surgical cue sheet data, may determine a cause of the bleeding based on the analysis result and may provide the cause.

Specifically, the computer analyzes a completed actual surgical cue sheet to search for a surgical error (S640). When a surgical error situation is detected according to a preset rule, the computer may provide the feedback indicating the surgical error.

For example, a general surgical error situation and a method of providing the feedback accordingly are as described below.

In an example, the computer may detect an event when a foreign object remains in the patient's body, the computer may provide a feedback indicating the event. According to a disclosed embodiment, the computer recognizes all objects included in the surgical image, as well as a location of the surgical tool, and the bleeding site, based on the obtained surgical image, and analyzes each of the objects. The computer determines a location, numbers, and an invasion time of the objects included in the surgery image. Therefore, the computer may generate a warning when it is determined that the foreign substance introduced into the surgery target portion has not been removed when the surgery is completed, and may provide a feedback that asks the user to check the surgery target portion. In one embodiment, the computer may ask the user to check the surgery target portion even when the object introduced into the surgery target portion is not identified in the image. For example, when it is not confirmed that the object that has invaded into the surgery target portion is removed from the surgery target portion, the object may not be included in the surgery image, but may remain at an invisible site. Thus, the computer may provide the feedback to ask the user to check the surgery target portion even when the object introduced into the surgery target portion is not identified in the image.

In one example, the computer may detect a surgical operation event of a wrong patient, and may provide a feedback indicating the event. According to a disclosed embodiment, the computer analyzes the surgery image in real time, and performs registration between organs in the 3D modeled image and actual organs. The computer tracks locations of the camera and surgical tool in real time, and determines a surgery situation and obtains information that a simulator follows in the actual surgical process. In one embodiment, when the actual organ and the organ in the 3D modeled image do not match with each other in a process of performing the registration between the patient's actual organ and the organ in the 3D modeled image, the surgery may be performed on the wrong patient. Thus, the computer may ask the user to check this situation.

In an example, the computer may detect a surgical operation event of a wrong surgical target portion, and may provide a feedback indicating the event. According to a disclosed embodiment, the computer determines a surgical situation, and provides a surgical guide image according to a rehearsal result or an optimal surgical scheme. In this process, when a process of the actual surgery is different from the rehearsal result or the optimal surgery scheme, the surgery may be performed on a wrong site or a different type of surgery may have been performed. Thus, the computer may ask the user to check this situation.

In an example, the computer may recognize a situation of nerve damage and may provide a feedback indicating this situation. In a disclosed embodiment, when the actual surgery is different from the rehearsal process, as described above, the computer may provide a feedback indicating this situation. When an important nerve or ganglion is cut depending on a positional relationship between the patient's organ and the surgical tool or when a risk that the surgical tool approaches the nerve is predicted, a warning may be provided to the user. Further, the computer visually presents a blood vessel, a nerve, and a ganglion that are invisible in an overlapping manner with the surgical image using image registration and AR (augmented reality) or MR (mixed reality) technology. Thus, even after the surgery, the user may see an important body portion well, thereby helping to review the surgical process.

Further, in another embodiment, the method may further include adding the actual surgical cue sheet data to the to-be-learned cue sheet data used for calculation of the optimized cue sheet data, and performing reinforcement learning (S660).

In one embodiment, the actual surgical cue sheet data may be improved compared to the optimized cue sheet data. Therefore, the actual surgical cue sheet data may be added to the to-be-learned cue sheet data and then the reinforcement learning thereof may be performed, thereby to obtain a model capable of creating improved optimized cue sheet data.

Further, in another embodiment, the computer tracks prognosis of the patient corresponding to each surgical record (S680). The computer may perform machine learning using each surgery record and the prognosis corresponding to each surgery record as to-be-learned data, thereby determining a combination of surgical operations resulting in each prognosis.

For example, the computer may analyze the surgical operations of patients with specific side effects, and thus the computer may derive detailed surgical operations or combinations of detailed surgical operations that may cause even minor surgical side effects.

In one embodiment, the computer may acquire information about detailed surgical operations that bring about each prognosis via the reinforcement learning. For example, the computer may perform the reinforcement learning based on operations performed in the surgical process, and learned data about prognosis occurring when the operations are included or are performed in a specific order. Based on the reinforcement learning result, the computer may determine what prognosis (i.e., what side effect) may occur due to a specific detailed surgical operation, continuous detailed surgical operations, or a combination of detailed surgical operations.

Further, the computer may output and provide the feedback to the user in various ways. In one embodiment, the computer may extract detailed surgical operations having defects and provide the extracted detailed surgical operations as the feedback. For example, the computer may extract and reproduce only images of the detailed surgical operations having the defects, thereby to help the user to grasp the defects.

Further, the computer may search for and provide detailed surgical operations included in the surgical process. For example, the surgery is usually performed for several hours or more, such that it is difficult for the user to check an entire surgery image after the surgery for feedback. Therefore, the computer may provide the cue sheet data. When the user selects one or more detailed surgical operations included in the cue sheet data, the computer may extract only the selected detailed surgical operation and may provide the feedback related thereto. For example, the computer may extract and reproduce only images of the selected detailed surgical operations.

According to a disclosed embodiment, each detailed surgical operation has a standardized name and standardized code data. Therefore, the user may search for each detailed surgical operation based on the standardized name or the standardized code data. The user may look at the cue sheet data to easily check the progress of the surgery.

The method for providing the feedback on the surgical outcome according to one embodiment of the inventive concept as described above may be implemented using a program (or application) to be executed in combination with a computer as hardware and stored in a medium.

The program may include codes coded in computer languages such as C, C++, JAVA, and machine language that a processor (CPU) of the computer may read through a device interface thereof, in order for the computer to read the program and execute methods implemented using the program. The code may include a functional code related to a function defining functions required to execute the methods, and an execution procedure-related control code necessary for the processor of the computer to execute the functions in a predetermined procedure. Moreover, the code may further include a memory reference-related code indicating a location (address) of an internal memory of the computer or an external memory thereto in which additional information or media necessary for the processor to execute the functions is stored. Moreover, when the processor of the computer needs to communicate with any other remote computer or server to execute the functions, the code may further include a communication-related code indicating how to communicate with any other remote computer or server using a communication module of the computer, and indicating information or media to be transmitted and received during the communication.

The storage medium means a medium that stores data semi-permanently, rather than a medium for storing data for a short moment, such as a register, a cache, or a memory, and that may be readable by a machine. Specifically, examples of the storage medium may include, but may not be limited to, ROM, RAM, CD-ROM, a magnetic tape, a floppy disk, and an optical data storage device. That is, the program may be stored in various recording media on various servers to which the computer may access or on various recording media on the user's computer. Moreover, the medium may be distributed over a networked computer system so that a computer readable code may be stored in a distributed scheme.

The steps of the method or the algorithm described in connection with the embodiments of the inventive concept may be implemented directly in hardware, a software module executed by hardware, or a combination thereof. The software modules may reside in random access memory (RAM), read only memory (ROM), erasable programmable ROM (EPROM), electrically erasable programmable ROM (EEPROM), a flash memory, a hard disk, a removable disk, CD-ROM, or any form of a computer readable recording medium well known in the art.

According to the disclosed embodiment, the feedback on the course and the outcome of the surgery may be provided to the user, based on the comparing result between the actual surgical process and the reference.

According to the disclosed embodiment, the feedback may be provided by extracting the necessary portion from the entire surgery image. Thus, even when the user does not look through the entire surgery image, the user may check the necessary portion thereof.

The effects of the inventive concept are not limited to the effects mentioned above. Other effects not mentioned will be clearly understood by those skilled in the art from the above description.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

REFERENCE NUMERALS

10: Medical imaging apparatus
20: Server
30: Controller
32: Display
34: Surgery robot
36: Imaging unit

What is claimed is:

1. A device for providing a feedback on a surgical outcome based on artificial intelligence, comprising:
an image sensor configured to capture a surgical image of an actual surgical process; and
a processor configured to:
generate actual surgical data based on the surgical image,
divide the actual surgical data into a plurality of detailed surgical operations to obtain actual surgical cue sheet data composed of the plurality of detailed surgical operations, obtain reference cue sheet data about the actual surgery, and provide feedback by comparing the actual surgical cue sheet data with the reference cue sheet data, wherein the reference cue sheet data includes at least one of optimized cue sheet data about the actual surgery and referenced virtual surgical cue sheet data, wherein the optimized cue sheet data includes cue sheet data calculated by an optimized surgical process by learning one or more cue sheet data, and wherein the reference cue sheet data includes cue sheet data for virtual surgery or actual surgery performed for constructing big data for learning or guiding a surgical process.

2. The device of claim 1, wherein the actual surgical data is divided into the plurality of detailed surgical operations, based on at least one of a surgery target portion, a type of surgical tool, a number of surgical tools, a position of the surgical tool, an orientation of the surgical tool, and movement of the surgical tool included in the actual surgical data.

3. The device of claim 1, wherein at least one of a standardized name and standardized code data is assigned to each of the plurality of detailed surgical operations.

4. The device of claim 1, wherein the processor is further configure to determine whether at least one surgical error is included in the actual surgical cue sheet data by comparing the plurality of detailed surgical operations included in the actual surgical cue sheet data with a plurality of detailed surgical operations included in the reference cue sheet data, and wherein the at least one surgical error includes at least one of an unnecessary detailed surgical operation, a missing detailed surgical operation, and an incorrect detailed surgical operation.

5. The device of claim 4, wherein the processor is further configured to determine whether a detailed surgical operation included in the actual surgical cue sheet data is incorrect by comparing motion of surgical tool corresponding to a detailed surgical operation included in the reference cue sheet data with motion of surgical tool corresponding to the detailed surgical operation included in the actual surgical cue sheet data.

6. The device of claim 1, wherein the processor is further configured to:

detect an occurrence of an event from the actual surgical data, determine a cause of the event by analyzing a detailed surgical operation before occurring the event included in the actual surgical cue sheet data, and wherein the event includes at least one of bleeding information, foreign object information and nerve damage information.

7. The device of claim 1, wherein the processor is further configured to obtain optimized cue sheet data for each situation classified according to a physical condition and a surgical target portion condition when obtaining the reference cue sheet data.

8. The device of claim 1, wherein the processor is further configured to:

add the actual surgical cue sheet data to to-be-learned cue sheet data, and perform reinforcement learning on a model for the obtaining optimized cue sheet data using the to-be-learned cue sheet data.

9. The device claim 1, wherein the processor is further configured to:

obtain information about prognosis corresponding to each of one or more actual surgical cue sheet data including the actual surgical cue sheet data, perform reinforcement learning based on information about the one or more actual surgical cue sheet data and the prognosis, and determine a correlation between at least one detailed surgical operation included in the one or more actual surgical cue sheet data and the prognosis based on a result of the reinforcement learning.

10. The device claim 1, further comprising:

a display; and wherein the processor is further configured to:

extract a first image of one or more detailed surgical operation corresponding to a situation of surgical error or a second image of one or more detailed surgical operation including a situation of event, and play the first image or the second image through the display.

11. A method for providing a feedback on a surgical outcome based on artificial intelligence, performed by a device, the method comprising:

capturing, by an image sensor of the device, a surgical image of an actual surgical process;

generating, by a processor of the device, actual surgical data based on the surgical image;

dividing, by the processor, the actual surgical data into a plurality of detailed surgical operations to obtain actual surgical cue sheet data composed of the plurality of detailed surgical operations;

obtaining, by the processor, reference cue sheet data about the actual surgery; and providing, by the processor, feedback by comparing the actual surgical cue sheet data with the reference cue sheet data, wherein the reference cue sheet data includes at least one of optimized cue sheet data about the actual surgery and referenced virtual surgical cue sheet data, wherein the optimized cue sheet data includes cue sheet data calculated by an optimized surgical process by learning one or more cue sheet data, and wherein the reference cue sheet data includes cue sheet data for virtual surgery or actual surgery performed for constructing big data for learning or guiding a surgical process.

* * * * *